(12) United States Patent
Yau et al.

(10) Patent No.: US 6,580,249 B2
(45) Date of Patent: Jun. 17, 2003

(54) INTELLIGENT SERIAL BATTERY CHARGER AND CHARGING BLOCK

(75) Inventors: Kwok Wong Yau, Tsuen Wan (HK); Yiu Cheung Li, Sham Tseng (HK); Long Bai, Buji (CN)

(73) Assignee: GPE International Limited, New Territories (HK)

( * ) Notice: Subject to any disclaimer, the term of this patent is extended or adjusted under 35 U.S.C. 154(b) by 0 days.

(21) Appl. No.: 09/971,593

(22) Filed: Oct. 9, 2001

(65) Prior Publication Data

US 2003/0042870 A1 Mar. 6, 2003

(30) Foreign Application Priority Data

Sep. 3, 2001 (HK) .......................... 01106195

(51) Int. Cl.$^7$ ................................................. H02J 7/00
(52) U.S. Cl. ..................................................... 320/122
(58) Field of Search ................................ 320/120, 122; 307/54, 60, 63, 77, 100, 125; 361/88

(56) References Cited

U.S. PATENT DOCUMENTS

| | | | |
|---|---|---|---|
| 4,303,877 A | 12/1981 | Meinhold | 320/122 |
| 4,626,764 A | 12/1986 | Weinhardt | 320/107 |
| 4,719,401 A | 1/1988 | Altmejd | 320/122 |
| 4,961,157 A * | 10/1990 | Nick et al. | 320/115 |
| 5,099,188 A | 3/1992 | Birnbreier et al. | 320/127 |
| 5,270,635 A | 12/1993 | Hoffman et al. | 320/122 |
| 5,650,240 A | 7/1997 | Rogers | 429/61 |
| 5,675,233 A | 10/1997 | Kaneko et al. | 320/163 |
| 5,744,936 A | 4/1998 | Kawakami | 320/120 |
| 5,804,944 A | 9/1998 | Alberkrack et al. | 320/163 |
| 5,850,136 A | 12/1998 | Kaneko | 320/119 |
| 5,923,150 A * | 7/1999 | Umetsu | 320/162 |
| 5,998,967 A | 12/1999 | Umeki et al. | 320/122 |
| 6,025,696 A | 2/2000 | Lenhart et al. | 320/122 |
| 6,034,506 A | 3/2000 | Hall | 320/117 |
| 6,046,514 A | 4/2000 | Rouillard et al. | 307/77 |
| 6,121,752 A | 9/2000 | Kitahara et al. | 320/122 |
| 6,211,650 B1 | 4/2001 | Mumaw et al. | 320/122 |
| 6,265,846 B1 | 7/2001 | Flechsig et al. | 320/116 |
| 6,271,646 B1 | 8/2001 | Evers et al. | 320/122 |
| 6,329,792 B1 * | 12/2001 | Dunn et al. | 320/132 |

FOREIGN PATENT DOCUMENTS

| | | |
|---|---|---|
| CN | 1138768 A | 12/1996 |
| CN | 1164771 A | 11/1997 |
| CN | 2384357 Y | 6/2000 |
| EP | 0798841 A2 | 10/1997 |

OTHER PUBLICATIONS

Maxim Integrated Products, "*MAXIM NiCd/NiMH Battery Fast–Charge Controllers*", Jan. 1997, 18 pps.

\* cited by examiner

*Primary Examiner*—Edward H. Tso
*Assistant Examiner*—Pia Tibbits
(74) *Attorney, Agent, or Firm*—Burns, Doane, Swecker & Mathis, L.L.P.

(57) ABSTRACT

A serial battery charger including a number of serially connected battery charging sections in which the battery charging section is characterized by a first and second parallelly connected branches. The first branch includes terminals for connecting to the battery to be charged and a current blocking device and the second branch includes a by-passing switch which shunts across the terminals of the first branch when activated. The blocking device in the first branch prevents adverse reverse current flow from the battery to the charger when there is no power supply and also functions as a current block to prevent adverse flow of current from the battery into the shunting by-passing switch when the power supply to the charging section is in operation. This invention provides a simple solution to fulfil the conflicting requirements of an intelligent serial battery charger.

14 Claims, 4 Drawing Sheets

INTELLIGENT SERIAL BATTERY CHARGER AND CHARGING BLOCK

This application claims priority under 35 U.S.C. §§119 and/or 365 to 01106195.9 filed in Hong Kong on Sep. 3, 2001; the entire content of which is hereby incorporated by reference.

FIELD OF THE INVENTION

The present invention relates to battery chargers for charging a plurality of rechargeable batteries connected in series. More particularly, this invention relates to battery chargers having a plurality of serially connected battery charging sections. More specifically, although not solely limiting thereto, this invention relates to serial battery chargers in which a battery in any one of the serially connected charging sections can be removed or bypassed without materially affecting the charging conditions of the batteries remaining in other charging sections of the serial battery charger. Furthermore, this invention relates to serial battery chargers in which there is utilized a simple electronic element which provides a low-impedance to the charging circuit during charging, a high-impedance to block reverse current flow from a battery when there is no power supply to the charging section and a comparatively high-impedance when the charging section is shunted or by-passed.

BACKGROUND OF THE INVENTION

Re-chargeable batteries are widely used in a lot of portable or mobile electrical and electronic devices or appliances such as, cellular or cordless telephones, remote repeaters, remote control units, remote sensors, portable lighting devices, portable radios, portable drills and many other devices. Re-chargeable batteries are generally preferred over disposable batteries nowadays because they are more environmental friendly and provide longer term cost savings. For remote applications, rechargeable batteries are probably the only practical choice.

Re-chargeable batteries require repeated charging in order to supply electrical power to the devices or appliances in which they are installed. Nowadays, portable devices usually require a plurality of batteries to operate and the batteries required are typically in the range of two to ten batteries. Hence, it is desirable that there can be provided intelligent battery chargers which can charge a plurality of re-chargeable batteries at the same time. There are two main types of battery chargers. The first type is the parallel charger in which all the batteries are subject to the same charging voltage but are charged with different charging currents. The other type is the serial charger in which the batteries being charged are connected in series and the same charging current usually passes through all the serially connected batteries.

In applications in which batteries are alternatively charged and discharged, a power supply of 3 to 12 volts is generally required while the voltage of each rechargeable battery is typically in the region of 1–2 volts. In those applications, batteries are typically connected in series for charging and discharging. For charging batteries for use in such applications, a serial battery charger must be used.

Because of the wide-spread use of rechargeable batteries, there are increasing demands for fast battery chargers which are capable of fully charging an empty battery in about an hour (the "1C" chargers) so that users do not have to wait for too long before the batteries are sufficiently charged for use. For example, for a 1,600 mAH re-chargeable battery, the 1C current rate is about 1.6A. In order to facilitate fast and efficient battery charging, battery chargers generally utilise high frequency pulsed charging current having a relatively high current rate. When a battery is being charged, it will produce oxygen on the electrode and the consumption of oxygen by the negative electrode will cause the battery to heat up. In general, charging at the current rate of 1C is preferred because this charging rate is regarded as striking a balance between reducing charging time and maintaining a healthy battery under current battery technologies. Of course, with further advance in battery technologies, batteries may be charged at even higher current ratings without over-heating. If that happens, battery chargers supplying higher charging rating than 1C will be expected to become more popular. In general, fast battery chargers, especially those for charging small voltage re-chargeable batteries of about 1.5–2V, are preferably configured so that the batteries are charged in series. This is because if the batteries are fast charged in parallel, a power supply having a very large current supply rating will be required and this may be very costly.

On the other hand, a serial connection implies that the same current must flow through each serially connected charging section. This may also create great difficulty in a lot of circumstances. For example, when a battery is removed from the charger upon completion of charging to avoid overheating or damaging or because it is already defective, charging will be disrupted until a replacement battery has been inserted into the charger. Similar problems also arise if rechargeable batteries of different capacities are charged together or good batteries are mixed with bad ones. This is because when a battery of a smaller capacity has been fully charged, there is a good chance that a battery of a larger capacity still requires charging. For simple serial chargers with no monitoring and control circuits, the batteries will be continuously charged. As a result, overheating, battery damage or even explosion may result. On the other hand, for those more sophisticated serial battery chargers with charging conditions monitoring and charge control circuits, the battery charger may shut down once any one of the batteries being charged is detected as being fully charged. This is obviously undesirable as the remaining batteries may still require further charging. Furthermore, whenever batteries are inserted or removed from a serial battery charger during the charging process, the whole charging process will be interrupted. Hence, it is desirable if there can be provided intelligent serial battery chargers which allow serial charging of re-chargeable batteries in which the charging currents supplied to the individual batteries in serial connection are largely independent of that supplied to other batteries.

For many battery chargers, it is known that, when power supply to the battery charger is turned off, there may be a reverse leakage current which flows from the battery to the charger or the peripheral circuitry. Reverse leakage current among the serially connected batteries could also cause reverse charging of individual batteries by other batteries that are connected in the series charger. This is clearly undesirable which may cause draining of the full battery capacity and may even damage the charger. Hence, it is desirable that each charging section of a serial battery charger is provided with means to prevent undesirable reverse current leakage as well as a by-passing circuitry so that the charging conditions of one individual charging section would not affect the charging conditions of the other charging sections.

Many by-passing circuits, circuit arrangements or topologies have been proposed to alleviate the adverse influence of the charging conditions in a serial charging section to other charging sections. While serial chargers having arrangements to by-pass some or all of the charging sections have been known, they are generally very complicated and do not simultaneously include means or circuits to prevent reverse leakage or discharge from the batteries.

To provide a serial battery charger which fulfils the above requirements is a difficult task because several conflicting requirements need to be met. Firstly, in order to prevent reverse current leakage or adverse current discharge from the battery, a blocking device which has a high reverse impedance must be inserted in series with the battery. Secondly, that serial block device must have a low impedance when there is a forward current which flows into the battery for battery charging. On the other hand, if the blocking device has a low forward impedance when the by-passing switch has been activated (which usually occurs when there is still power supply to the battery charging terminals), that low-impedance blocking device will compete with the by-passing switch for the supplied current and, as a result, adverse charging current will keep flowing into the batteries. In addition, that blocking device must have a high impedance when the by-passing switch has been activated, otherwise, a large and un-desirable current will flow in a current loop which is formed by the battery, the blocking device and the by-passing switch. Hence, it is highly desirable if a serial battery charger which can fulfil the above conflicting requirements can be provided. It will be even more desirable if such improved battery chargers can be realised using simple circuit blocks and components so that high reliability as well as low costs can be achieved.

OBJECT OF THE INVENTION

It is therefore an object of the present invention to obviate the problems or shortcomings associated with existing or known serial battery chargers. In particular, it is an object of the present invention to provide a circuit arrangement for an improved battery charging section which can be used in serial chargers so that the charging section can be shunted or by-passed when selected and, at the same time, providing blocking means to prevent reverse current.

An important objective of the present invention is therefore to provide an intelligent serial battery chargers in which the charging current or charging conditions of one battery in the serial connection is largely unaffected by the charging conditions of other batteries in the serial connection.

An equally important object of the present invention is to provide a serial battery charger in which a battery can be removed from the serially connected battery at any time without disrupting the charging of other batteries and, at the same time, adverse reverse current flow from a battery can be avoided.

As a minimum, it is an object of the present invention to provide the public with a choice of serial battery chargers which are provided means to obviate undesirable battery discharge when the battery charger is not supplying charging power and to provide useful battery by-pass when necessary.

SUMMARY OF THE INVENTION

According to the present invention, there is provided an improved serially connected battery charger which includes at least first and second parallelly connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and it has a high-impedance when said by-passing switch is turned on.

According to another aspect of the present invention, there is provided a charging block for use in a serial battery charger including at least first and second parallelly connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and a high-impedance when said by-passing switch is turned on.

According to a third aspect of the present invention, there is provided a serial battery charger including a battery charging section which includes at least first and second parallely connected branches, wherein said first branch includes a diode serially connected with the terminals for connecting the battery to be charged and said second branch includes a MOSFET by-passing switch, said by-passing switch is connected across said first branch and provides low-impedance shunting when activated, said blocking diode has a low-impedance when current flows into said battery to be charged and has a high-impedance when there is no power supply from said battery charger or when said by-passing switch is turned on.

According to a fourth aspect of the present invention, there is provided a battery charger including a plurality of battery charging sections which are connected in series, wherein each said charging section includes a first and a second parallely connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and it has a high-impedance when said by-passing switch is turned on.

Preferably, the battery charger further including a micro-controller, the micro-controller monitors a set of parameters of the battery being charged and activates said by-passing switch by forming a low-impedance shunting across said first parallel branch when some or all of said measured battery parameters satisfies a set of pre-determined conditions.

Preferably, the one-way electronic device is a diode.

Preferably, the by-passing switch is a field-effect-transistor ("FET"), including a MOSFET.

Preferably, the gate of said by-passing MOSFET is connected to a microcontroller which controls the gate voltage of said MOSFET to turn on or turn off said MOSFET such that when said MOSFET is turned on, the impedance across the drain-source terminals of said MOSFET is low, thereby activating the by-passing function, and, when said MOSFET is turned off, the impedance across the drain-source terminals is very high, thereby de-activating the by-passing function.

BRIEF DESCRIPTION OF THE DRAWINGS

Preferred embodiments of the present invention will be explained in further detail by way of example and with reference to the accompanying drawings. In which.

DETAILED DESCRIPTION OF THE PREFERRED EMBODIMENT

Figure 1:
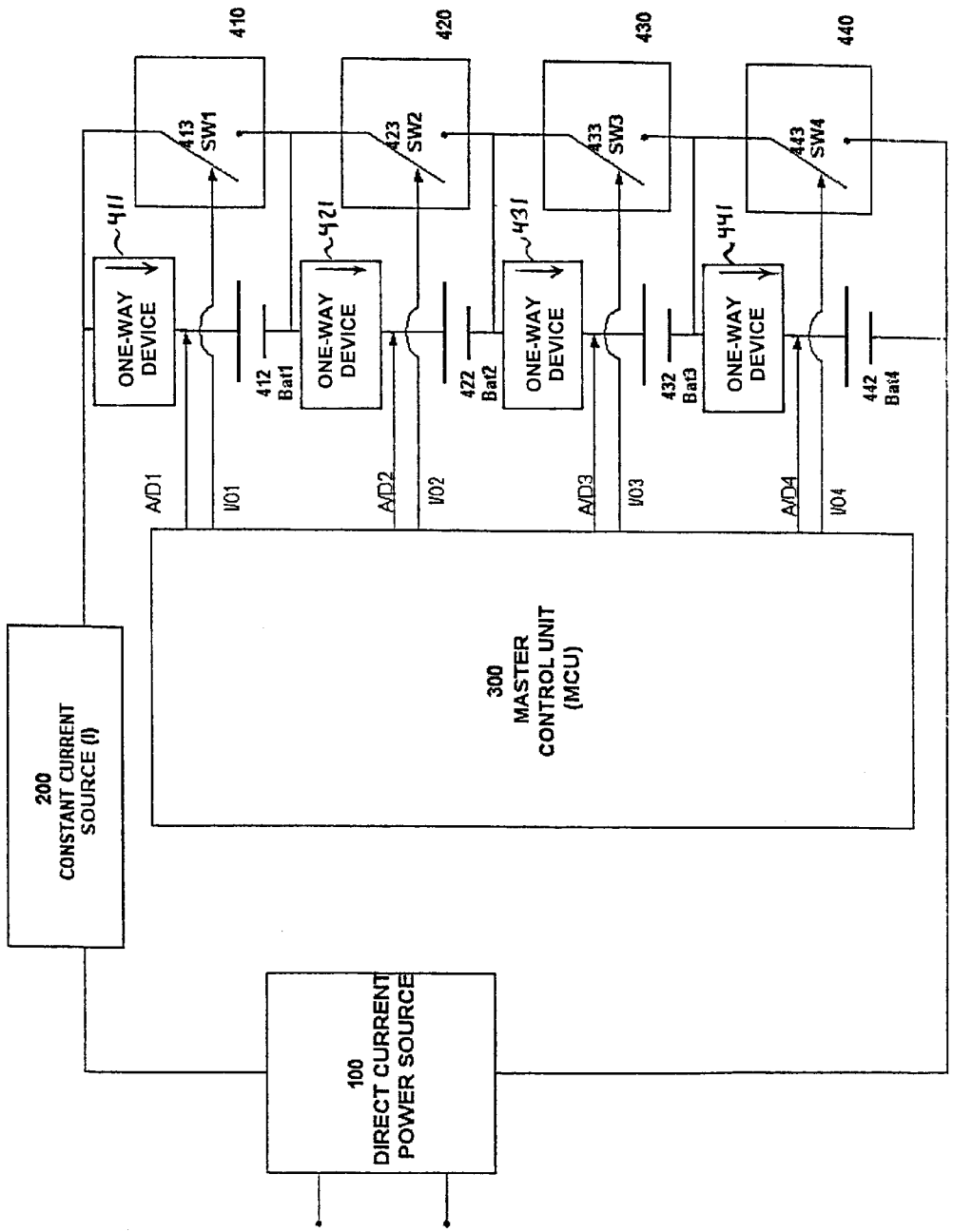
FIG. 1 is a general block circuit diagram of the serial battery charger of a preferred embodiment of the present invention.

Referring to FIG. 1, there is shown a block diagram showing a first example of a preferred embodiment of the present invention of an intelligent serial battery charger. The battery charger includes a direct current power source (100), a constant current source (200), a micro-controller unit (300) and plurality of battery charging sections (410, 420, 430 and 440) connected in series. The serially connected battery charging sections are connected to the positive and negative terminals of the direct current power source (100) in order to obtain DC power of the correct polarity.

Referring to FIG. 1, each of the charging sections (410, 420, 430 and 440) includes an one-way electronic device which is connected in series with the positive and negative terminals of the battery in order to control charging connecting to a battery. In order to provide a controllable by-passing path which provides low impedance shunting across a charging section when necessary, for example, when the battery in a particular charging section is fully charged, defective or overheated, there is provided an electronic controllable switch (413) as shown in the Figure. The by-passing switch is connected in parallel with the serial connection of the battery terminals and the one-way electronic device. The by-passing switch provides low impedance shunting across the terminals of the serial connection of the one-way electronic device and the battery terminals when activated. In the present specific embodiments, the by-passing switch is a three-terminal device in which the impedance across two of its terminals is controllable by a third terminal.

The one-way electronic device which is inserted in series with the battery under charge should endeavour to fulfil the following conflicting requirements. Firstly, it is preferred to have a low-impedance when the battery is being charged (that is, when forward current flows into the battery). Secondly, it is preferred to have a high-impedance when there is no power supply from the charger or, in other words, when the voltage at the battery terminals exceeds that of the charging terminals in order to prevent adverse discharge or reverse current flow from the battery, otherwise, the batteries will be drained when there is no power supply from the direct current power source (100). Thirdly, the blocking device should have a very high impedance when the by-passing switch has been turned on because, otherwise, a current loop which is formed by the battery, the one-way device and the by-passing switch, may cause burning out of the circuit, since the by-passing switch should be of low-impedance in nature and the resulting current in the current loop will be very large. In addition, the blocking device should have a considerably higher impedance than that of the activated by-passing switch (i.e. when it has been turned on) when the by-passing switch has been activated and when the voltage at the charging terminals exceeds that of the battery, so that adverse current will not flow into the battery through the one-way electronic device.

In addition to merely providing a by-passing path, the combination of the electronically controllable by-passing switch together with the one-way electronic device allows high frequency and repeated open-circuit measurements across the battery terminals to be taken. Such open-circuit measurements are preferred in order to obtain sufficient battery parameters to assess the charging conditions of a battery. An example of how the open-circuit electrical parameters of the batteries can be taken will be explained below. For example, when the micro-controller (300) needs to read the open-circuit parameters of the battery (422) which is being charged in the second serial charging block (420), it sends out electronic control signals through its I/O ports to the control terminals of the three-terminal by-passing switches and turns on the by-passing switches 413, 433 and 443. As a result, the impedance across the two other terminals of the by-passing switches 413, 433 and 443 will be very low and the batteries 412, 432 and 442 will be substantially by-passed because of the high impedance of the blocking device in this circumstances.

When the by-passing switches 413, 433 and 443 have been activated, a measurement of the voltage taken across the positive terminal (A/D2 in FIG. 2) of the second battery (422) and the ground will give the characteristics of battery 422 only, since all the other batteries, namely, 412, 432 and 442, have been isolated from the measurement circuitry because of the isolation by the blocking devices 411, 431 and 441. It will be noted that, at this instant, the one-way electronic devices 411, 431 and 441 will isolate the batteries 412, 432 and 442 from the charging section and the open-circuit parameters of the battery 422 can then be measured.

After measurements have been taken, the micro-controller again sends out another control signal to the electronically controlled three-terminal switches 413, 433 and 443 so that the impedance across the two other terminals of the by-passing switches will again resume a high state to de-activate by-passing. As a result, current flows again through the one-way electronic device into the batteries being charged.

Alternatively, the second battery (422) can be measured by having the second by-passing switch (423) activated. At this instant, the second battery will be isolated and measurement can be taken across the battery terminals directly. Of course, additional analogue-digital converters will be needed to measure the potential difference across the two battery terminals. To ensure accurate measurement of the open-circuit parameters, it is highly desirable that when the by-passing switches are closed (activated), no current flows in or out of the batteries the associated by-passing switches of which have been activated, otherwise, the open-circuit readings will not be accurate.

In order to prevent current from flowing out of the battery when open-circuit or close-circuit measurements are to be taken, the one-way electronic device should have a very high impedance which is sufficient to prevent current from flowing out of the battery in the reverse direction when by-passing is activated, even if the voltage at the terminals of the charging section before and after the activation of the by-passing switch is higher than that of the battery. Simultaneously, it is also preferred to prevent or minimise the current which may flow into the battery terminals when the by-passing switch is turned on (or closed or activated, at which point the impedance across the two terminals of the by-passing switch is in the low state).

To prevent adverse flow of current from the power source into the battery when the by-passing switch is closed, the impedance of the one-way electronic device (411, 421, 431, 441) when the by-passing switch is closed should be significantly higher than that of the by-passing switch (413, 423, 433, 443). On the other hand, the one-way electronic device should have a very low-impedance where there is current supply from the charger and when the by-passing switch is opened so that the charging current will entirely flow into the battery via the one-way electronic device for charging. To provide an electronically controllable switch which has a high and a low-impedance state, a MOSFET is selected. In general, when a suitable gate voltage is applied to a MOSFET, the drain-source terminals of the MOSFET will become conducting with low-impedance. On the other hand, if a different gate voltage is applied, the drain-source terminals of the MOSFET will have a very high-impedance and become non-conducting. A MOSFET switch is selected as a by-passing switch because it has a relatively high bandwidth so that the by-passing switch can be turned on and off many times within a short period of time. Such repeated switching is required in order to take all the necessary open circuit measurements and readings. The high bandwidth is also preferred in order to take responsive action once any abnormality of a battery is observed and in order to minimise any noticeable disruption to the other charging sections when a battery is removed from the charger. Of course, other electronic devices exhibiting similar electronic characteristics may also be used as alternatives.

As regards the one-way electronic device, MOSFET also appeared to be a suitable candidate. In experiments to use a MOSFET as the one-way device, the micro-controller was programmed so that opposite effect gate voltages are sent to the MOSFETs (one as one-way device and the other as by-passing switch). With such an arrangement, when one MOSFET is on, the other will be off and vice versa. Hence, when the one-way device is turned on, a low impedance path will be provided for the charging current. When the by-passing MOSFET is on, the one-way device will be off, thereby forming a high impedance serial resistor isolating the battery from the rest of the circuit.

Figure 2:
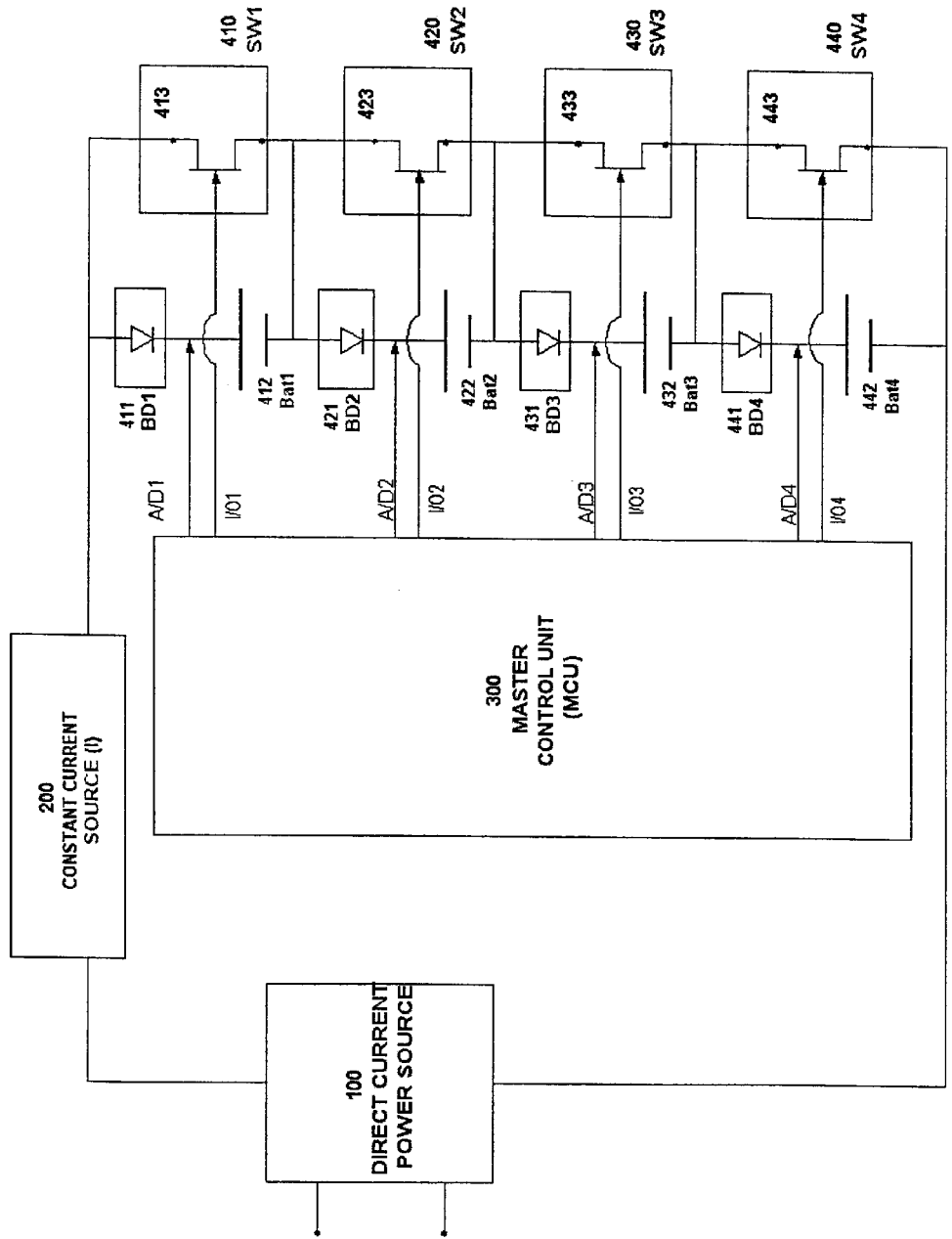
FIG. 2 is a block diagram showing a specific example of the components used in each of the serial charging sections.

Referring to FIG. 2, there is shown a preferred embodiment of the present invention in which a specific combination of an one-way electronic device and a by-passing switch are shown. In this embodiment, a MOSFET is used as a by-passing switch and a diode is used as an one-way electronic device. The diode is connected in series with the battery terminals in the manner as shown in FIG. 2 so that charging current can flow into the battery through a low-impedance path while reverse current flow is blocked. When the MOSFET by-passing switch (413, etc.) is turned on, the drain-source impedance becomes very low and the drain-source voltage is therefore also very low which is typically in the region of 0.2 volt. Since such a low voltage across the drain and source terminals is far from the turn-on voltage of the diode which is typically in the region of 0.6 volt, the diode becomes a high-impedance blocking device which prevents current from flowing into the battery. By the synergetic utilization of the combined characteristics of the two devices, namely, the low drain-source voltage of about 0.2 volt when a MOSFET is turned on and the high turn-on voltage of about 0.6 volt for a diode, a battery charger or battery charging section satisfying the afore-said conflicting requirements can be provided. As shown in the Figures, a plurality of charging sections can be connected in series in order to provide a preferred serial charger.

Figure 3:
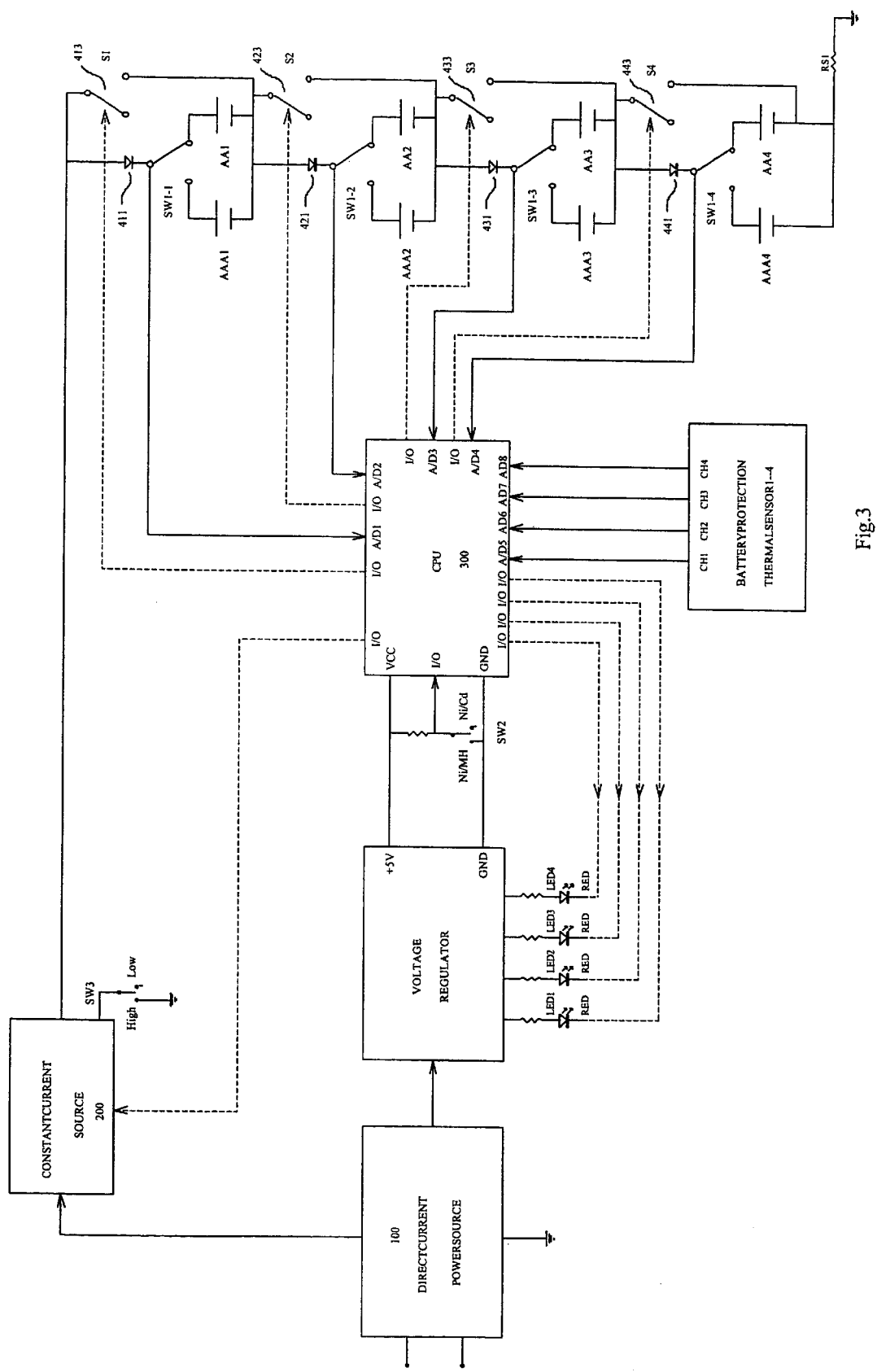
FIG. 3 is a general circuit diagram showing more connection particulars of the serial battery charging of FIGS. 1 and 2.

Referring to FIG. 3, there is shown a schematic diagram showing more detailed connection between the power source (100), current source (200), CPU (300) and the serially connected charging sections (410, 420, 430, 440). Each of the charging section includes a blocking diode (411, etc.) which prevents reverse flow of current out of the battery as well as providing a high-impedance isolation of the battery terminals when the low-impedance switch (413, etc.) is turned on, even though at that instant, the diode is under a small forward bias. In this specific embodiment and as shown in FIG. 3, each charging section is provided with receptacles for alternatively charging a AAA or a AA battery.

Figure 4:
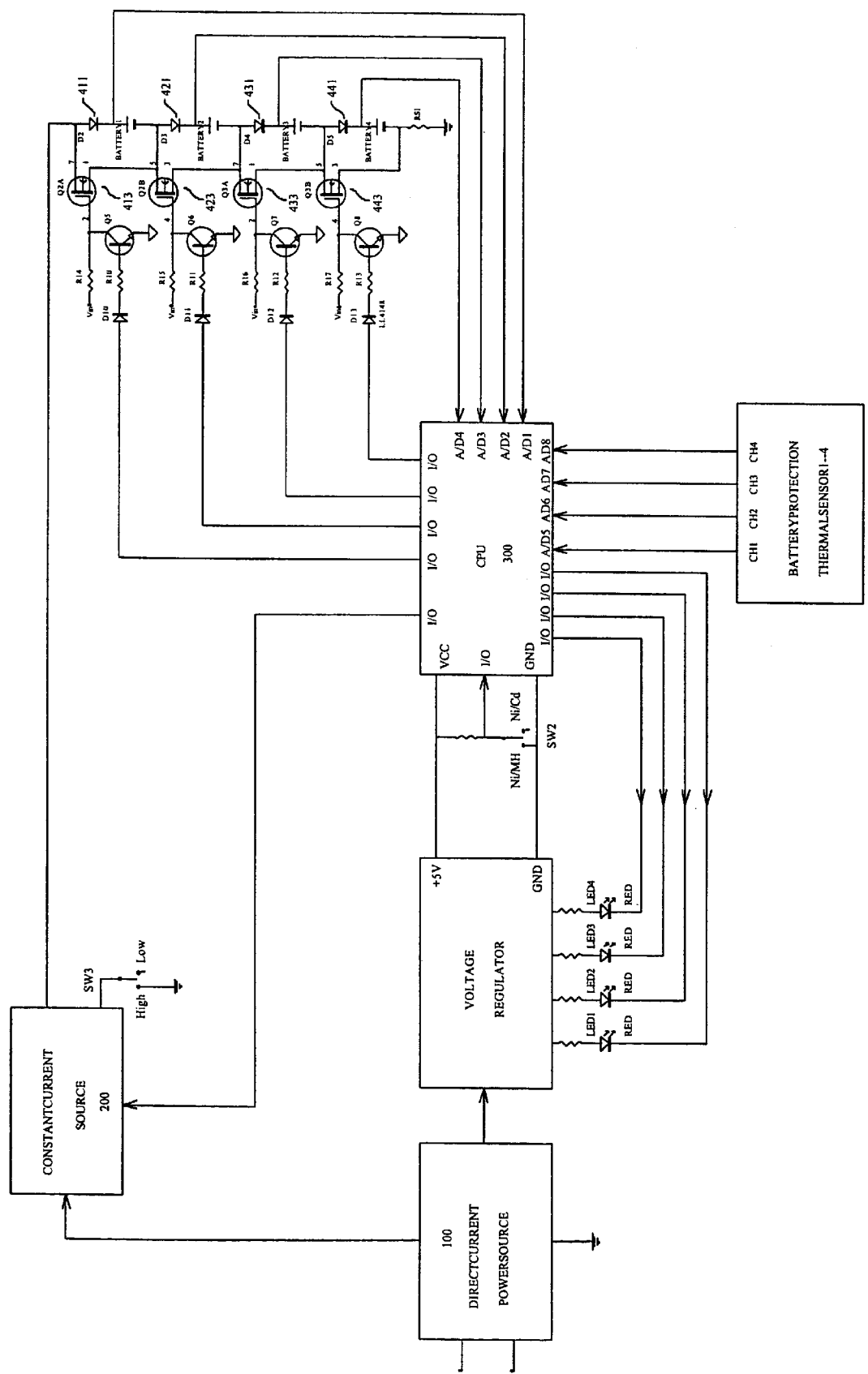
FIG. 4 is a general circuit diagram showing more detailed hardware connection of a preferred embodiment of the present fast serial battery charger.

Referring to FIG. 4, there is shown a more detailed circuit arrangements of the charging sections of FIG. 3. In this specific embodiment, the by-passing MOSFETs, the blocking diodes as well as the MOSFET gate controlling circuitry which is connected between the by-passing MOSFETs and the CPU is described in more detail. This gate control circuitry is intended to provide only a working example of the control of the by-passing switch, many other circuit variations are of course possible to achieve substantially same or similar effects.

While the present invention has been explained by reference to the various specific examples described above, it should be appreciated that those examples are merely provided to assist understanding only and should not in any way be used to limit or restrict the scope of the present invention. In addition, it should be appreciated that the scope of the present invention shall be interpreted according to the spirit of the invention as described in the above description and should therefore cover modifications or variations which are obvious or trivial to persons skilled in the art. In particular, the present invention has disclosed a synergetic utilization of a combination of rather simple components to proffer a circuitry or circuit arrangements in which the various conflicting requirements for battery charging sections are accommodated and provided in a very simple way and by using relative simple components and in a simple arrangement.

What is claimed is:

1. A serial battery charger including a charging section which includes at least first and second parallelly connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and it has a high-impedance when said by-passing switch is turned on.

2. A battery charger according to claim 1, further including a micro-controller to monitor at least one parameter of the battery being charged and activate said by-passing switch by forming a low-impedance shunting across said first parallel branch when one or more of said measured battery parameters satisfies a pre-determined condition.

3. A battery charger according to claim 2, wherein said battery parameter include any one or more of the following parameters:-open-circuit voltage, close-circuit voltage and the temperature of said battery.

4. A battery charger according to claim 3, wherein said battery parameters further include the detection of the type and presence of a battery.

5. A battery charger according to claim 1, wherein said one-way electronic device is a diode.

6. A battery charger according to claim 1, wherein said by-passing switch is a field-effect-transistor ("FET"), including a MOSFET.

7. A battery charger according to claim 6, wherein said gate terminal of said FET is connected to said micro-controller for activating and de-activating said by-passing switch.

8. A charging block for use in a serial battery charger including at least first and second parallelly connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and a high-impedance when said by-passing switch is turned on.

9. A charging block according to claim 8, further including a micro-controller to monitor at least one parameter of the battery being charged and activate said by-passing switch by forming a low-impedance shunting across said first parallel branch when one or more said measured battery parameters satisfies a pre-determined condition.

10. A serial battery charger including a battery charging section which includes at least first and second parallely connected branches, wherein said first branch includes a diode serially connected with the terminals for connecting the battery to be charged and said second branch includes a MOSFET by-passing switch, said by-passing switch is connected across said first branch and provides low-impedance shunting when activated, said blocking diode has a low-impedance when current flows into said battery to be charged and has a high-impedance when there is no power supply from said battery charger or when said by-passing switch is turned on.

11. A battery charger according the claim 10, wherein the gate of said by-passing MOSFET is connected to a micro-controller which controls the gate voltage of said MOSFET to turn on or turn off said MOSFET such that when said MOSFET is turned on, the impedance across the drain-source terminals of said MOSFET is low, thereby activating the by-passing function, and, when said MOSFET is turned off, the impedance across the drain-source terminals is very high, thereby de-activating the by-passing function.

12. A battery charger including a plurality of battery charging sections which are connected in series, wherein each said charging section includes at least first and second parallelly connected branches, said first parallel branch includes an electronically controllable by-passing switch and said second parallel branch includes positive and negative terminals for receiving respectfully the positive and negative terminals of a battery and an one-way electronic device connected in series, said by-passing switch has a very low impedance when turned-on and a very high impedance when turned-off, said one-way electronic device is characterised in that it has a very low-impedance when current flows from said charging section into said battery terminals and it has a high-impedance when said by-passing switch is turned on.

13. A battery charger according to claim 12, further including a micro-controller to monitor at least one parameter of the battery being charged and activate said by-passing switch by forming a low-impedance shunting across said first parallel branch when one or more of said measured battery parameters satisfies a pre-determined condition.

14. A battery charger according to claim 12, wherein said one-way electronic device is a diode.

* * * * *